United States Patent [19]

Pierce

[11] Patent Number: 5,324,308
[45] Date of Patent: Jun. 28, 1994

[54] SUTURE ANCHOR

[76] Inventor: Javin Pierce, 240 W. Canal St., Winooski, Vt. 05404

[21] Appl. No.: 142,058

[22] Filed: Oct. 28, 1993

[51] Int. Cl.⁵ ............................................. A61B 17/00
[52] U.S. Cl. ...................................... 606/232; 606/72; 606/77
[58] Field of Search ...................... 606/232, 72, 74, 75, 606/77, 86, 220; 411/456, 508, 509, 913

[56] References Cited

U.S. PATENT DOCUMENTS

| | | | |
|---|---|---|---|
| 4,716,893 | 1/1988 | Fisher et al. | 606/72 |
| 4,790,303 | 12/1988 | Steffee | 606/72 |
| 4,796,612 | 1/1989 | Reese | 606/72 |
| 4,870,957 | 10/1989 | Goble et al. | 606/232 |
| 4,898,156 | 2/1990 | Gatturna | 606/232 |
| 5,037,422 | 8/1991 | Hayhurst et al. | 606/232 |
| 5,102,421 | 4/1992 | Anspach, Jr. | 606/232 |
| 5,141,520 | 8/1992 | Goble et al. | 606/232 |
| 5,176,682 | 1/1993 | Chow . | |
| 5,236,431 | 8/1993 | Gogolewski et al. | 606/72 |

Primary Examiner—Stephen C. Pellegrino
Assistant Examiner—Gary Jackson
Attorney, Agent, or Firm—John J. Welch, Jr.

[57] ABSTRACT

The instant device is made up of a guide wire component, a proximal wedge component and a distal wedge component with the proximal wedge component having a side with an inclined medial face, two suture grooves on this side above its inclined face, a stop face inclined obtusely to and outwardly from its inclined face and a guide wire hole through its head extending through its length and terminating in its inclined face as well as serrated bone biting edges located on its opposite side and with the distal wedge component having two suture thread holes in its medial face and at its base and a guide wire hole on the side where its inclined face is found below and between its two suture thread holes and at its base, and a stop face inclined obtusely and inwardly from its inclined face as well as a beveled bone biting edge at its top such that simultaneous application of downward pressure on the head of the proximal wedge component and upward pressure on suture thread threaded through suture thread holes in the distal wedge component, after separation of those two components from the guide wire component subsequent to these two components having been guided along the guide wire previously placed into a hole previously drilled in bone, in the drilled hole in bone serves to firmly and permanently lodge these two components within the drilled hole in bone in order to permit the suture thread to be then tied to soft tissue to be thereby firmly anchored to the bone.

2 Claims, 8 Drawing Sheets

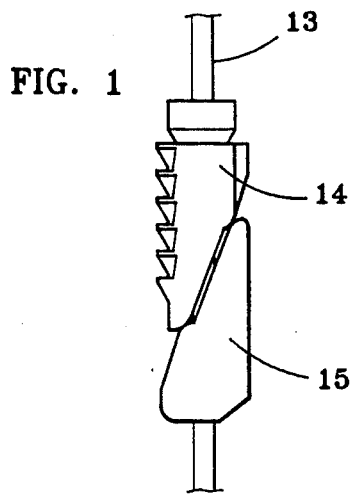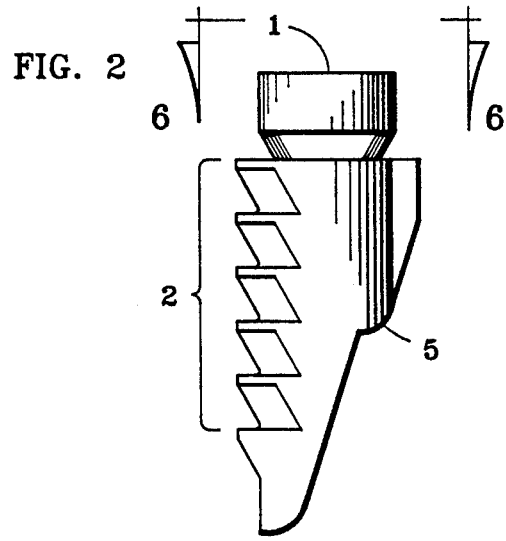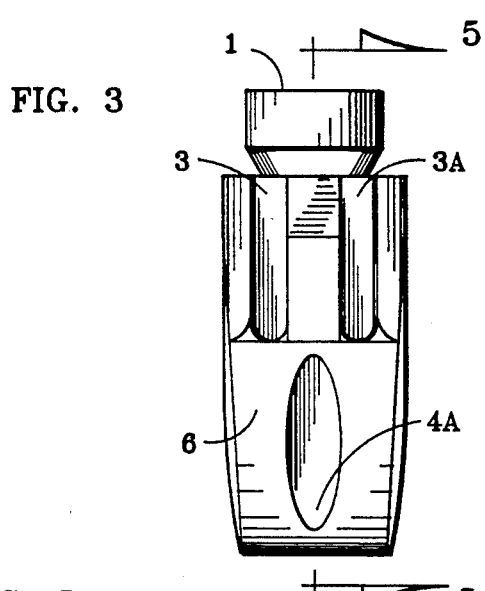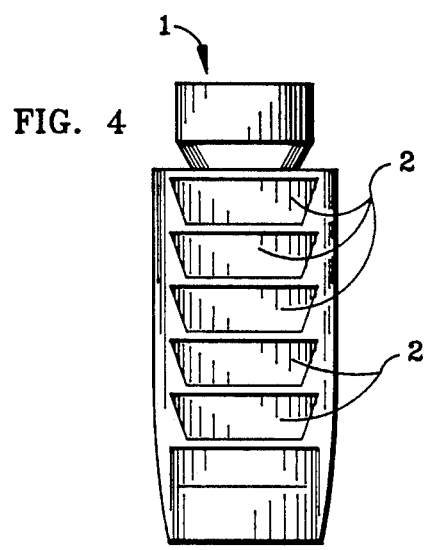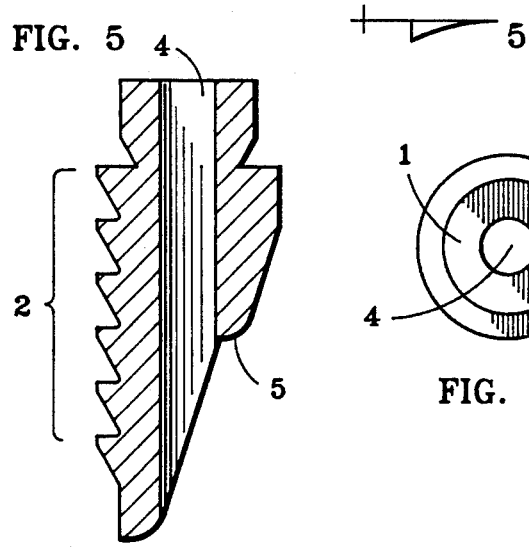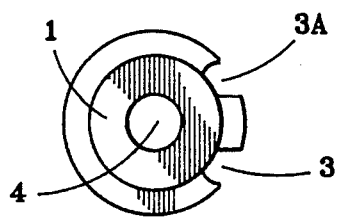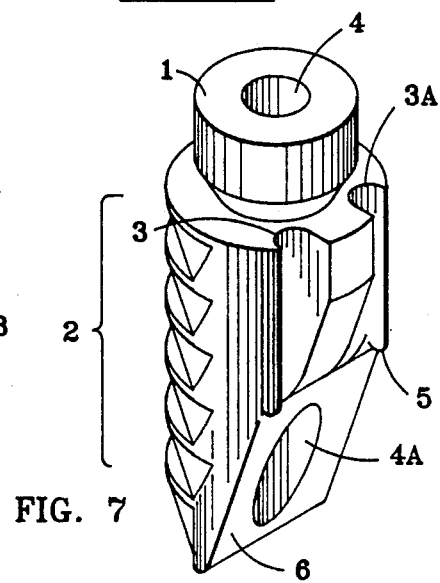

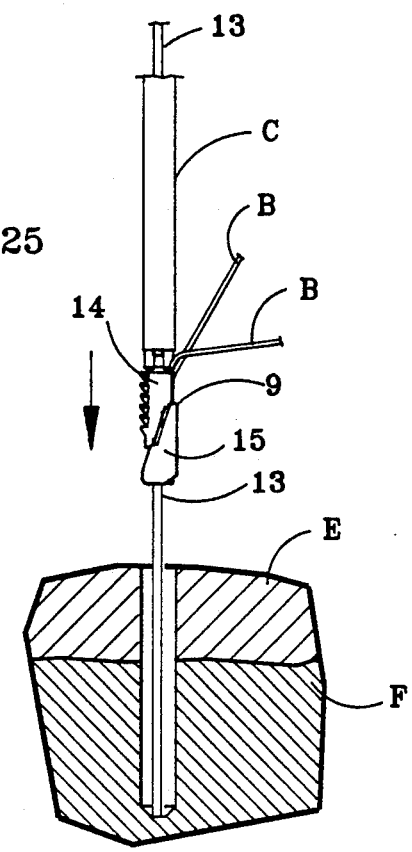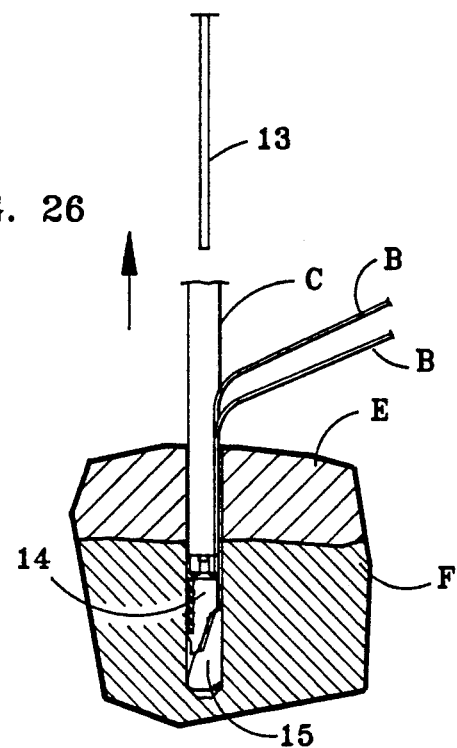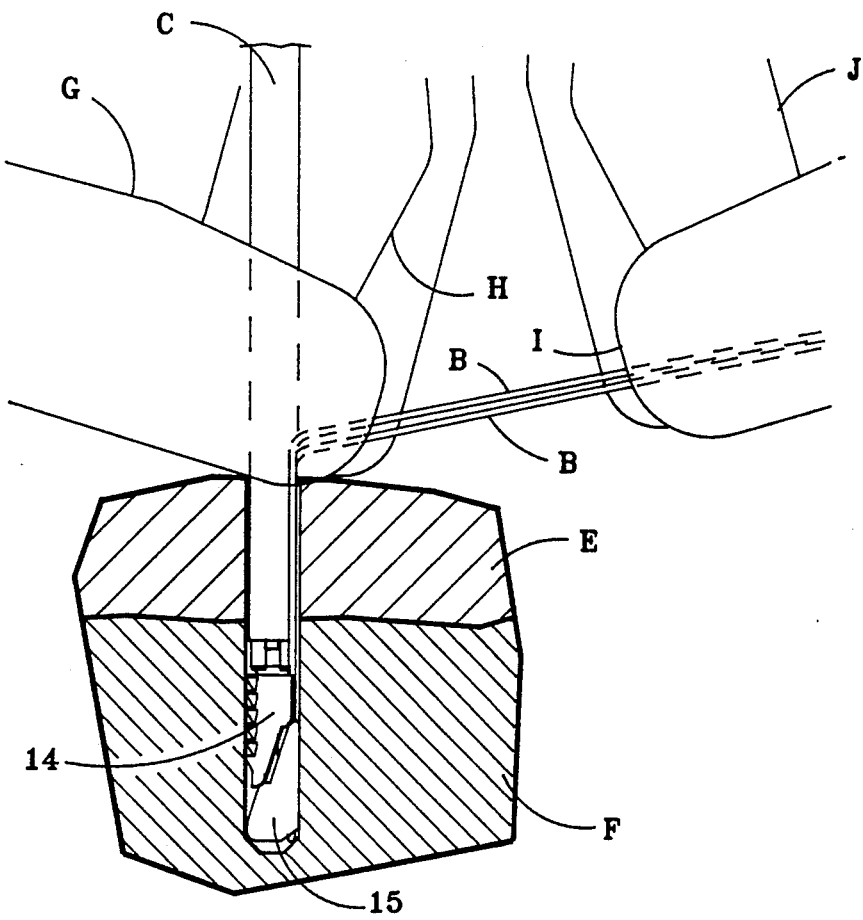

SUTURE ANCHOR

BACKGROUND OF THE INVENTION

1. Field of the Invention

The instant invention relates to that panoply of devices that serve to anchor to bone, suture materials for the purpose of facilitating adherence of soft tissues such as muscle and ligament tissues in close apposition to such bone by way of such suture materials being sewn thereto and therein.

2. Possible Prior Art

The following patents may bear somewhat on the essence of the instant invention. However, the instant invention represents a manifest improvement upon and variation from any other arguably similar devices current in or out of vogue within the scope of the field of such devices.

| Inventor | Invention | Pat. No. | Date |
| --- | --- | --- | --- |
| 1. Goble et al | Harpoon Suture Anchor | 5,141,520 | 8/25/92 |
| 2. Gatturna et al | Suture Anchor | 4,898,156 | 2/6/90 |
| 3. Chow | Surgical Implement | 5,176,682 | 1/5/93 |
| 4. Anspach, Jr. | Suture Anchoring and Method of Forming | 5,102,421 | 4/7/92 |
| 5. Fischer et al | Bone Fastener | 4,716,893 | 1/5/88 |
| 6. Goble et al | Ligament Anchor System | 4,870,957 | 10/3/89 |
| 7. Hayhurst et al | Bone Anchor and Method of Anchoring a Suture to a Bone | 5,037,422 | 8/6/91 |

SUMMARY OF THE INVENTION

1. A Description of the Invention

The instant invention is made up of three essential components. One is a so-called distal wedge. A second is a so-called proximal wedge. And, the third is a guide wire to which the first two components are fastened but amenable to removal therefrom.

A surgeon utilizes the invention by first resorting to utilization of a cannulated drill bit and drilling a hole into bone. Then the surgeon inserts the guide wire component of the instant invention through the lumen of the embedded drill bit after having first removed the drill therefrom by loosening the drill chuck and pulling the drill away. Once the guide wire is within the lumen of the bit, then the drill bit is removed by holding the guide wire with one hand and pulling out the bit with the other by way of a pincer device after having first removed the proximal wedge and distal wedge components from the guide wire component. Then the hand holding the guide wire above the removed bit is placed below the bit to continue holding the wire in place in the drilled hole while the bit is pulled up and off the wire. Then the wedge components are placed back on the guide wire after first threading suture wire through the distal wedge component and the wedge components are guided down the guide wire into the drilled hole and tamped down into place within the drilled hole. An insertion tool is utilized for such purpose. Then the guide wire component is removed from the drilled hole. Once the wedge components of the invention are in place, then downward pressure is applied to the head of the proximal wedge component by pushing down on it with the insertion tool to push it into the drilled hole while upward pressure is applied to the suture thread previously threaded through and about the base of the distal wedge. This combination of pushing and pulling causes the distal wedge to slide upwards against the proximal wedge being pushed downward. This action of sliding upward causes the inclined medial faces of each wedge component to slide over one another and to concomitantly push each wedge component laterally out against the sides of the drilled hole. The wedge components are thus pressed firmly and permanently into place by virtue of the increase in the central diameter of the two wedge components in interfaced apposition to one another in situ after application of the combined pressures of pushing down from the top and pulling up on the sutures about the bottom of the combined wedges. The lateral portion of the proximal wedge in-situ is made up of a set of serrated edges that bite into the bony side of the hole in apposition to it. The top portion of the body of the distal wedge is beveled so as to dig into the bony side of the hole in apposition to it. The medial portion of the proximal wedge in-situ has two suture grooves to accommodate suture material threaded through two cylindrical holes in the medial portion of the distal wedge in-situ. Suture material is threaded through one of these two cylindrical holes and out through a circular hole in the base of the distal wedge and then through a second circular hole in the base of the distal wedge and up through the body of the distal wedge and out the other of these two cylindrical holes. The base of the distal wedge component in the vicinity of the two holes in the base is inclined so as to prevent contact between suture thread passing from one circular hole to the other and the guide wire emanating from a third hole in the base. The proximal wedge has a round hole through its head and through its body running lengthwise that terminates in the inclined medial face in the lower portion of its body. This hole is the hole through which the guide wire component is initially threaded. The medial portion of the distal wedge in-situ has as well a hole in it, below the above-described two cylindrical suture holes, for receipt of the guide wire component that exits through the third hole in the base of the distal wedge.

The proximal wedge also has a stop face running out at a slightly obtuse angle from the angulation of its inclined medial face. This stop face by ultimately interfacing with a medially located distal wedge stop face prevents the distal wedge from sliding by the proximal wedge and thereby defeating the intended action of the two wedge components of the invention, to wit, permanent anchoring within a hole drilled in bone when upward pressure is applied to the suture thread by pulling the two ends of the thread upwards as downward pressure is applied to the head of the proximal wedge after the tamping down of the two wedges into the drilled hole. Upward pulling causes the stop face located on the medial aspect of the distal wedge to interface with the stop face of the proximal wedge to thereby prevent the distal wedge from sliding too far by the proximal wedge in-situ and thereby preventing the desired anchoring within bone.

2. The Object of the Invention

There are numerous and various types of anchor devices in existence today that are designed to facilitate the holding of soft tissue to bone by way of holding surgical sutures sewn into such soft tissue. But, these devices and means such as screws with loops on their crowns, glues and the like are universally amenable to failure over time due to, for example, degradation of bone, breakage at joints within such devices or adhesive defects. Such failure requires readmission of affected patients to surgery and subjugation of such persons to the inherent risks and inexorable expense related to the same. Hence, the essential object of the instant invention is to obviate, to the fullest possible extent, such failure.

The instant invention has no relatively delicate joint sites. It functions by way of action-reaction laterally directed and hence once wedged into place simply cannot come loose under the influence of whatever physiological load force as could conceivably be applied to it.

The instant invention is, respectfully submitted, in view of the foregoing, new, indeed revolutionary within its field and unquestionably useful and unique in that it functions in a truly new and unique way as a viable anchor. Moreover, in view of its new and unique type of framework, its dependability from a standpoint of essentially non-susceptibility to breakage in-situ is beyond reproach.

A DESCRIPTION OF THE DRAWINGS

FIG. 1 shows the three components of the instant invention, the proximal wedge component, the distal wedge component and the guide wire component in a perspective view.

FIG. 2 is a frontal view of the proximal wedge component of the instant invention that is indistinguishable from what would be a posterior view of this component.

FIG. 3 is a view of the medial side of the proximal wedge component of the instant invention in respect of its positioning in-situ within a hole drilled in bone.

FIG. 4 is a view of the lateral side of the proximal wedge component of the instant invention in respect of its positioning in-situ within a hole drilled in bone.

FIG. 5 is a longitudinal cross-sectional view of the proximal wedge component of the instant invention.

FIG. 6 is a top view of the proximal wedge component of the instant invention.

FIG. 7 is a perspective view of the proximal wedge component of the instant invention.

FIG. 25 shows the whole invention being inserted into a hole drilled in bone shown in cross-sectional view after removal of the drill bit and insertion of its guide wire component.

FIG. 26 shows the whole invention inserted into a hole drilled in bone shown in cross-sectional view subsequent to withdrawal of its guide wire component.

FIG. 27 shows a dotted facsimile of a surgeon's left index finger and thumb holding the insertion tool and pushing down on the invention within a hole in bone shown in cross-sectional view and a dotted facsimile of the surgeon's right index finger and thumb pulling up on suture thread.

Figure 28:
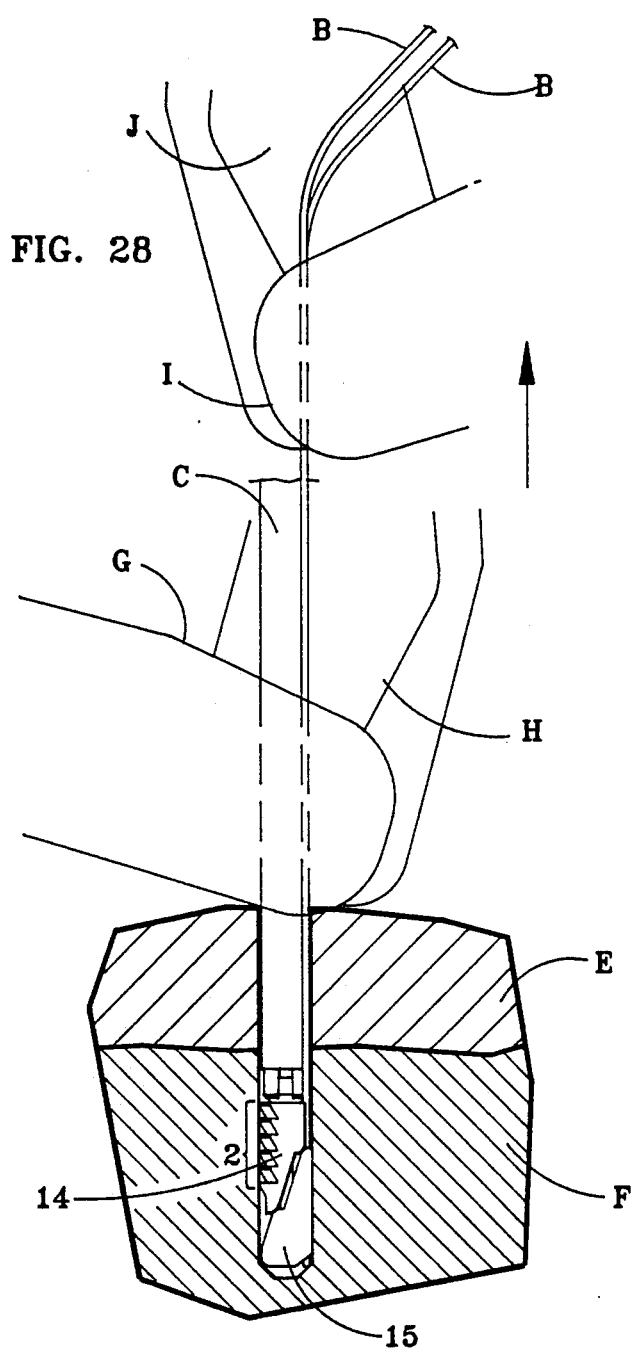

FIG. 28 shows a dotted facsimile of a surgeon's left index finger and thumb holding the insertion tool and pushing down on the invention within a hole in bone shown in cross-sectional view and a dotted facsimile of the surgeon's right index finger and thumb continuing to pull up on suture thread thereby causing the distal wedge component of the instant invention in-situ to rise against the proximal wedge component of the instant invention.

Figure 29:
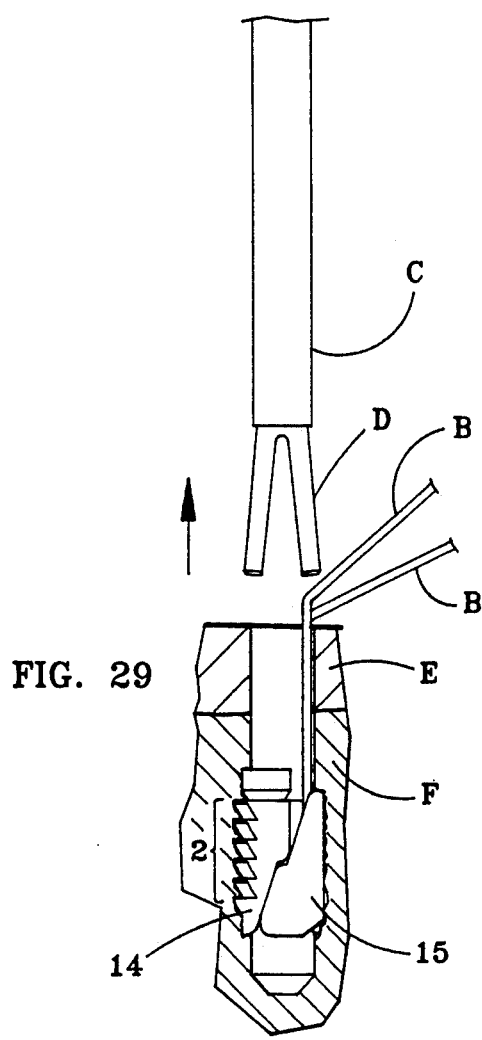

FIG. 29 shows the wedge components of the instant invention firmly in-situ within a hole drilled into bone subsequent to retraction of the insertion tool.

Figure 30:
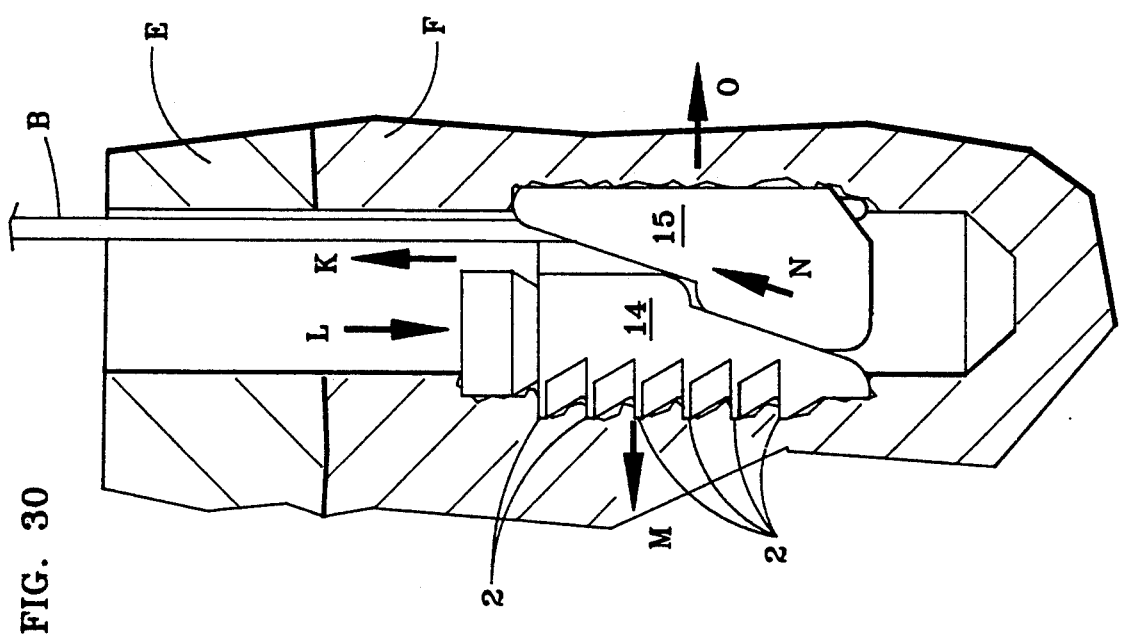

FIG. 30 is an enlarged view of the wedge components of the instant invention firmly in-situ. within a hole drilled into bone with arrows illustrating force vectors outwardly and laterally directed to the sides of the hole.

Figure 31:
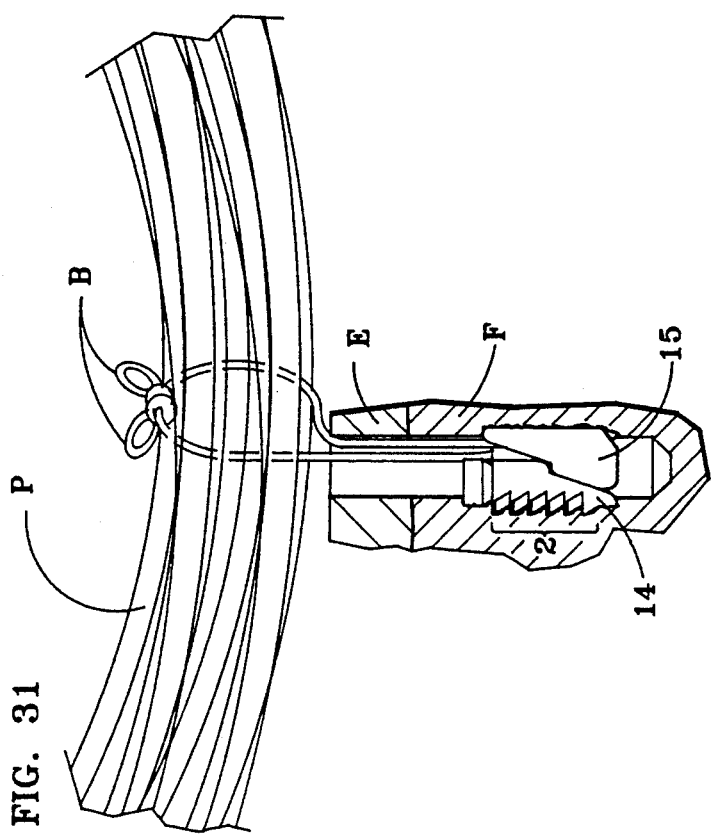

FIG. 31 a reduced view of FIG. 29 without arrows showing suture thread tied to soft tissue to be held in apposition to the bone.

A DESCRIPTION OF THE PREFERRED EMBODIMENT

Figure 8:
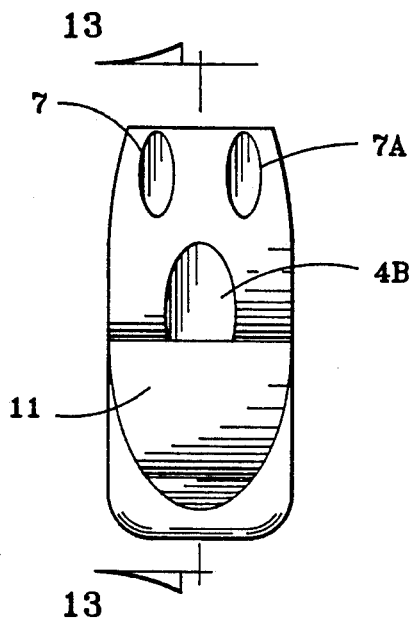
FIG. 8 is a view of the medial side of the distal wedge component of the instant invention in respect of its positioning in-situ within a hole drilled in bone.
Figure 9:
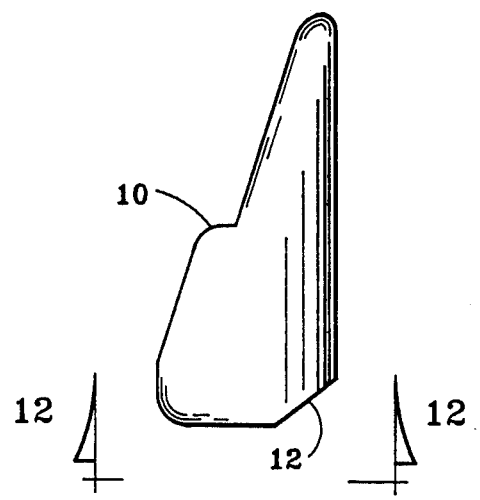
FIG. 9 is a frontal view of the distal wedge component of the instant invention that is indistinguishable from what would be a posterior view of this component.
Figure 10:
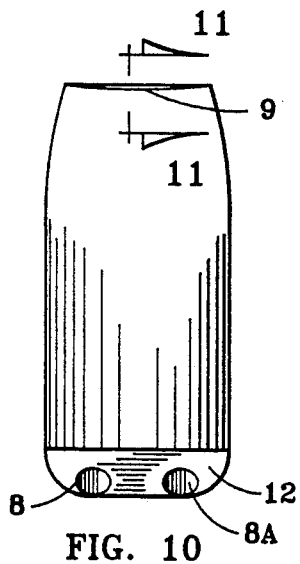
FIG. 10 is a view of the lateral side of the distal wedge component of the instant invention in respect of its positioning in-situ within a hole drilled in bone.
Figure 11:
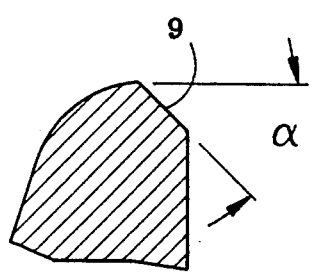
FIG. 11 is a cross-sectional cut away view showing the beveled edge of the top side of the distal wedge component of the instant invention.
Figure 12:
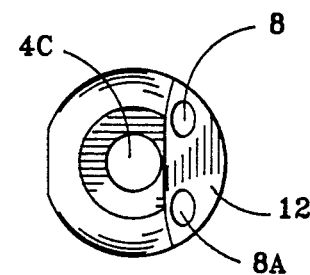
FIG. 12 is a bottom view of the distal wedge component of the instant invention.
Figure 13:
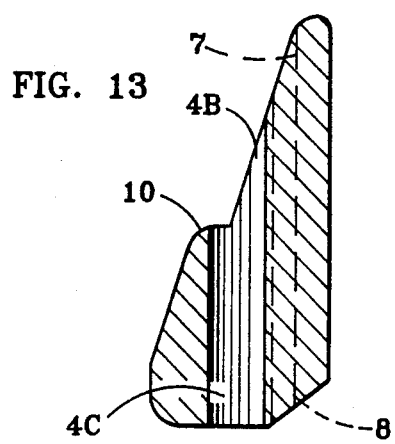
FIG. 13 is a longitudinal cross-sectional view of the distal wedge of the instant invention.
Figure 14:
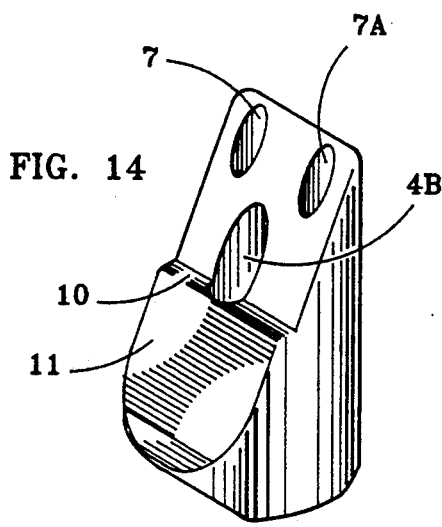
FIG. 14 is a perspective view of the medial side of the distal wedge component of the instant invention.
Figure 15:
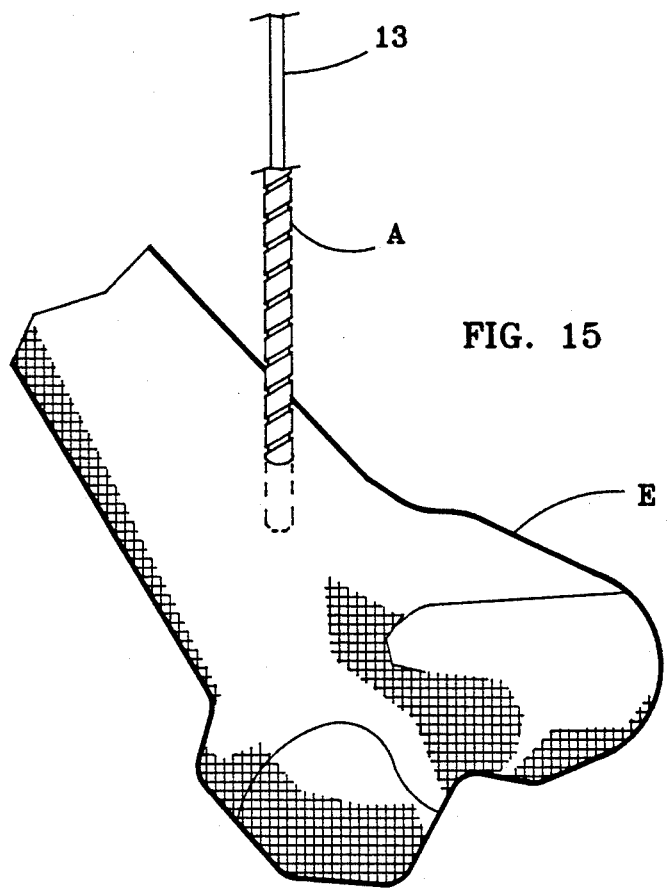
FIG. 15 shows a cannulated drill bit about to be drilled into bone.
Figure 16:
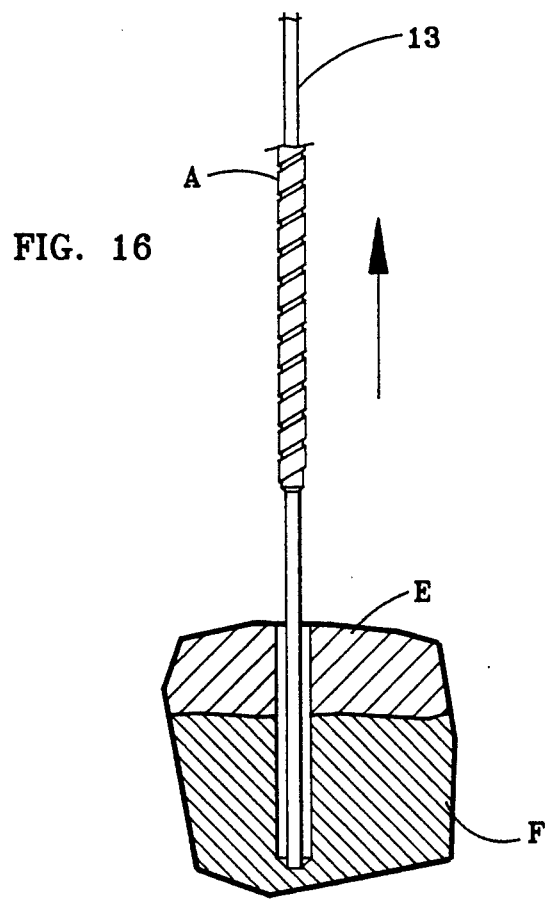
FIG. 16 shows a cannulated drill bit removed from bone after a hole has been drilled into the bone and the invention's guide wire component inserted through the bit into the hole.
Figure 17:
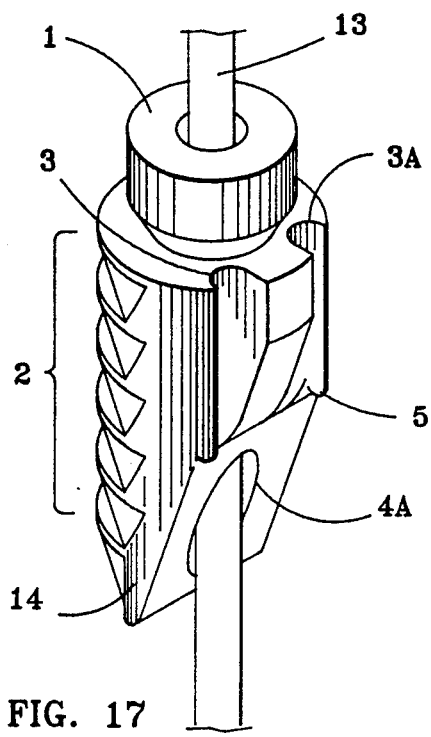
FIG. 17 shows the invention's guide wire component drawn through the proximal wedge component of the instant invention.
Figure 18:
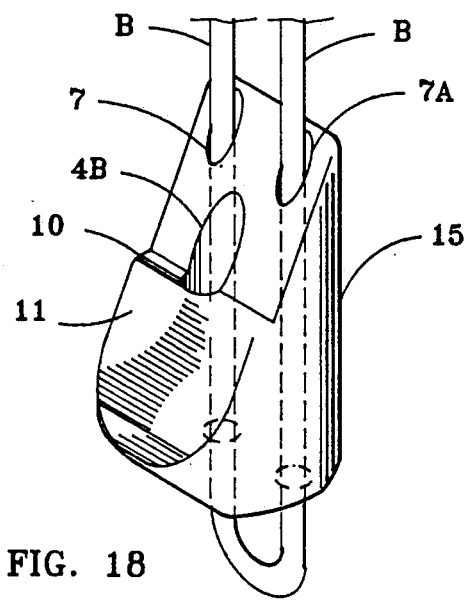
FIG. 18 shows suture thread through holes in the medial face and bottom of the distal wedge component of the instant invention.
Figure 19:
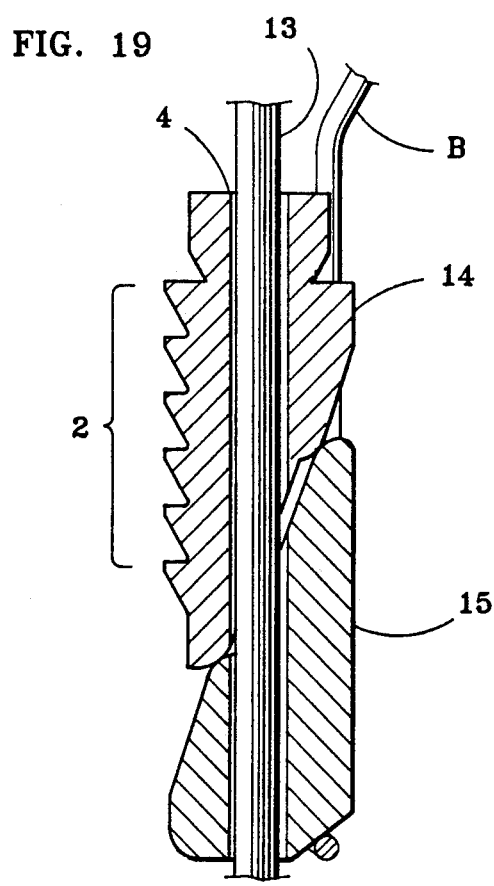
FIG. 19 is a longitudinal cross-sectional view of the proximal and distal wedge components of the instant invention through which its guide wire component and suture threads have been threaded.
Figure 20:
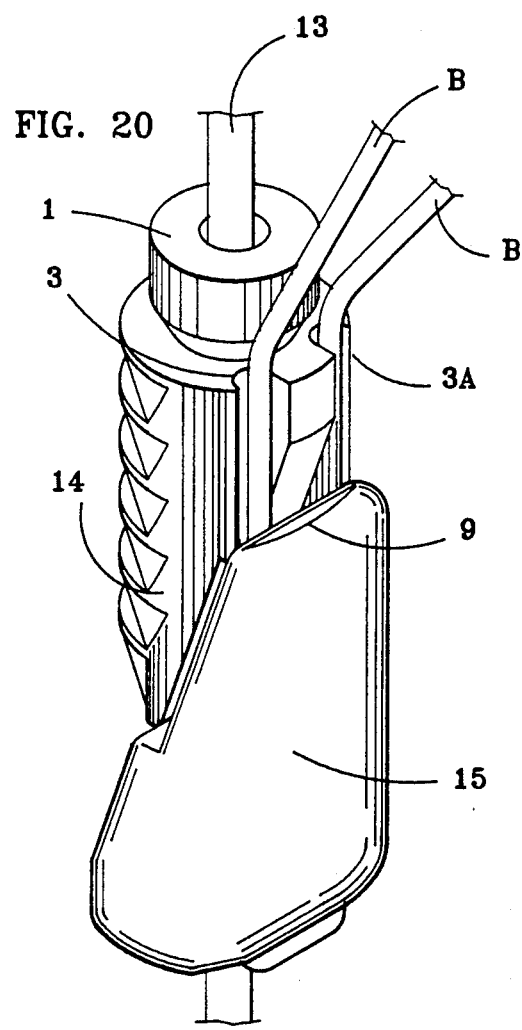
FIG. 20 is a perspective view of the proximal wedge component of the instant invention in apposition to a cut away view of the distal wedge component of the instant invention showing its guide wire component and suture threaded through the same.
Figure 21A:
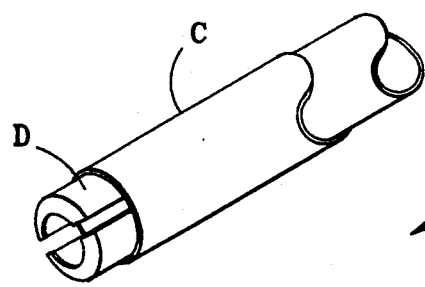
FIG. 21a is a perspective view of an insertion tool, to wit, a jaw within a sleeve.
Figure 21B:
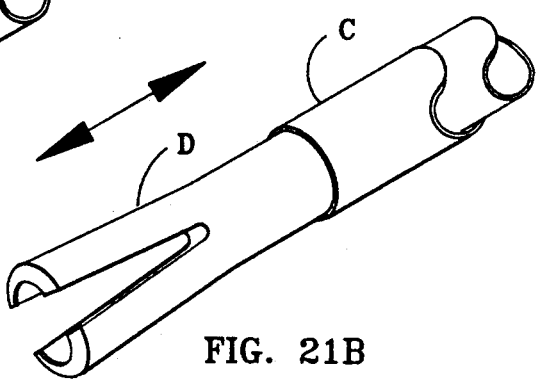
FIG. 21b is a perspective view of an insertion tool, to wit a jaw within a sleeve with the sleeve retracted to permit opening of the jaw closed only under the pressure of an overlapping non-retracted sleeve.
Figure 22:
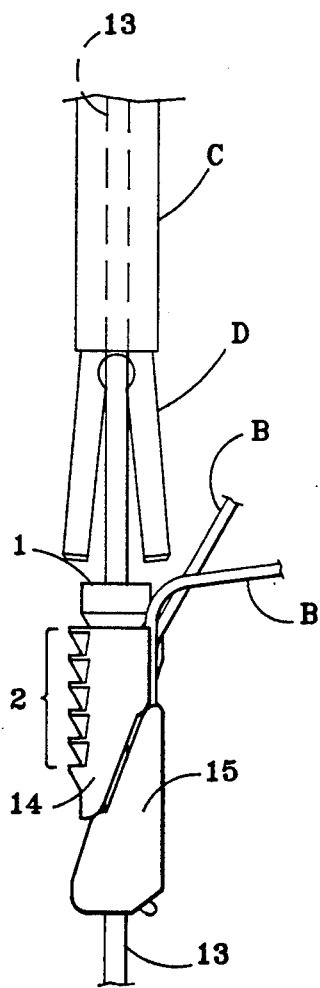
FIG. 22 is a view of the whole instant invention and suture thread in the presence of an insertion tool with retracted sleeve.
Figure 23:
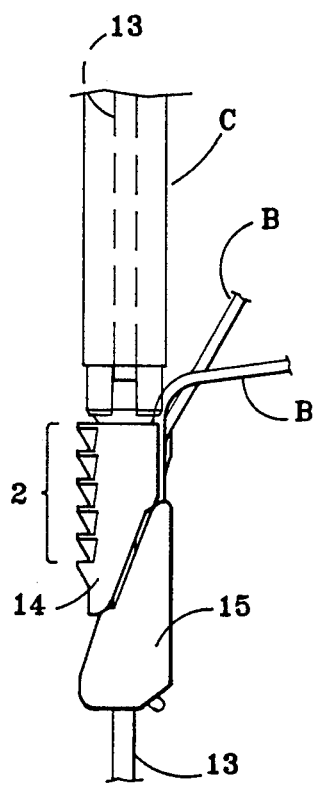
FIG. 23 is a view of the whole instant invention and suture thread in the presence of an insertion tool with non-retracted sleeve.
Figure 24:
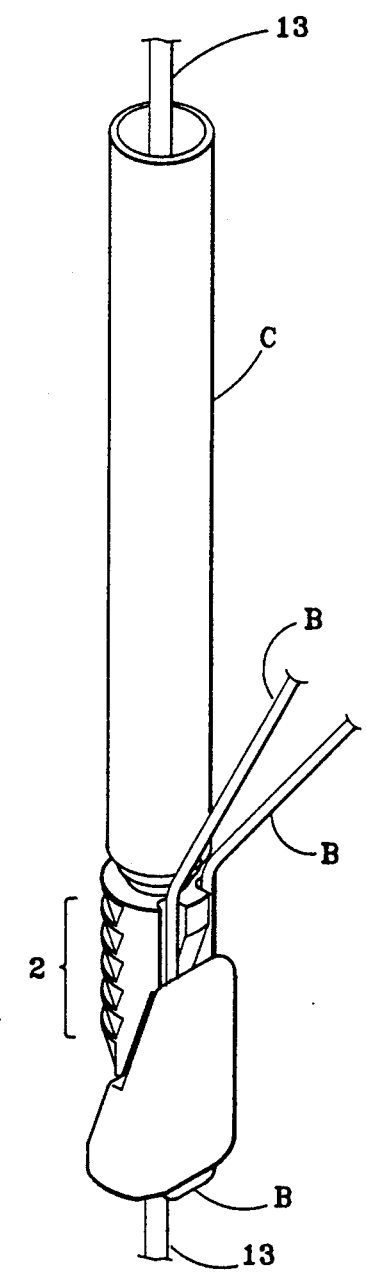
FIG. 24 is a perspective view of the whole instant invention and suture thread in the presence of an insertion tool with non-retracted sleeve.

FIG. 1 shows the three components of the invention, guide wire 13, proximal wedge component 14, and distal wedge component 15 fastened together to thus constitute the whole of the instant invention. FIG. 2 shows in frontal view the proximal wedge component 14 of the instant invention. Its cylindrically shaped head 1 is shown as well as its lateral side 2 in terms of how proximal wedge 14 is ultimately positioned as an anchor component within a hole drilled in bone which side 2 is made up of a plurality of serrated edges. Also shown is its stop face 5 extending at an obtuse angle out from the top of its inclined medial face 6 which face 6 is shown in FIG. 3 and again in FIG. 7. FIG. 3 shows two suture grooves 3 and 3a in the medial side of proximal wedge 14, to wit, the side of wedge 14 opposite in position to lateral side 2 once ultimately anchored in bone as well as a guide wire exit hole 4a in the medial face 6 of the proximal wedge. FIG. 4 shows lateral side 2 of proximal wedge 14 as well proximal wedge 14's cylindrically shaped head 1. FIG. 5 shows lateral side 2, guide wire hole 4 and stop face 5 of proximal wedge 14 in a longitudinal cross section view. FIG. 6 is a top view of proximal wedge 14 in which there is seen a top view of its cylindrically shaped head 1, guide wire entry hole 4 centrally located therein and a top view of proximal wedge 14's two identical suture grooves 3 and 3a. FIG. 7 is a perspective view of proximal wedge 14 wherein there is shown all of its features as depicted in FIGS. 2-6 inclusive. FIG. 8 is a view of the medial side of the distal wedge component 15 of the instant invention, to wit, that side of distal wedge 15 in apposition to the medial side of proximal wedge 14 once wedges 14 and 15 are firmly anchored in bone. Therein shown are two identical suture entry and re-exit holes 7 and 7a respectively as well as a guide wire entry hole 4b and its inclined medial face 11. FIG. 9 is a frontal view of distal wedge 15 in which there can be seen the lateral edge of its stop face 10. FIG. 10 is a plan view of the distal wedge 15 in which there is seen its beveled top edge 9 and two identical suture exit and re-entry holes, 8 and 8a respectively in the inclined face 12 of its base. FIG. 11 is a cross-sectional lateral view showing the beveled top edge 9 of distal wedge 15. It should be noted that the angle of beveling is constant to each of two points in the top edge of distal wedge 15 both equidistant from the center of the top edge from which points the angle of bevel tapers to zero degrees. FIG. 12 shows the inclined base face 12 of distal wedge 15 as well as guide wire exit hole 4c and suture exit hole 8 and suture re-entry 8a. FIG. 13 is a longitudinal cross-sectional view of distal wedge 15 showing its stop face 10, guide wire entry hole 4b, the canal therein leading therefrom to its guide wire exit hole 4c and dotted lines depicting the locus of the canal therein from its suture entry hole 7 to its suture exit hole 8. FIG. 14 shows distal wedge 15 in perspective view wherein there is to be seen its suture entry hole 7, its suture re-exit hole 7a, its guide wire entry hole 4b, its stop face 10 and its medial face 11. FIG. 15 is a view of a piece of bone E into which a hole is to be drilled with resort a cannulated drill bit A. Once a hole is drilled into bone E, the drill which was used is separated from the cannulated drill bit A and guide wire component 13 is threaded through the canal in drill bit A. Guide wire 13 is threaded down to the base of the drilled hole typically drilled deep enough into bone to pass into deep bone F below the outer cortex E of the bone. FIG. 16 shows in cross-sectional view, bone cortex E and a deeper layer F of bone. The arrow in FIG. 16 shows removal of the drill bit A from guide wire 13 after proximal wedge 14 and distal wedge 15 have first been removed therefrom prior to their being repositioned as they would be on guide wire 13 once drill bit A is fully removed therefrom. FIG. 17 shows guide wire 13 passing through guide wire entry hole 4 in the cylindrically shaped head 1 of proximal wedge 14 and out through its guide wire exit hole 4a. FIG. 18 shows suture thread B passing through suture entry hole 7 of distal wedge component 15 and down through the canal between hole 7 and suture exit hole 8 from which suture thread B emanates before reentering distal wedge 15 through suture re-entry hole 8a and passing up through the canal between hole 8a and suture re-exit hole 7a from which it emanates. FIG. 19 shows in cross-sectional view, guide wire 13 coursing through guide wire entry hole 4 in head 1 of proximal wedge 14 down through the canal therein leading from hole 4 to guide wire exit hole 4a and into guide wire entry hole 4b in distal wedge 15 and down through the canal therein leading from hole 4b to guide wire exit hole 4c in the base of the distal wedge. There is also to be noted in FIG. 19 suture thread B as it would be found passing via suture groove 3a found on the side of proximal wedge 14 opposite the lateral side 2 thereof and into suture entry hole 7 of distal wedge 15 and out suture exit hole 8 thereof. That which is depicted in FIG. 19 is depicted in part in FIG. 20 as well. FIG. 21A shows an insertion tool with a retractable sleeve C. FIG. 21B shows sleeve C of the insertion tool retracted so that its jaw D opens. FIG. 22 shows guide wire 13 threaded through the insertion tool and proximal wedge 14 and distal wedge 15 and coursing beyond them as it would be leading to the bottom of the previously drilled hole. FIG. 23 shows sleeve C of the insertion tool engaged over its jaw D in preparation for pushing down on head 1 of proximal wedge 14. FIG. 24 depicts in perspective view what is shown in FIG. 23. FIG. 25 shows guide wire component 13, proximal wedge 14 and distal wedge 15 components of the instant invention in apposition to the hole previously drilled into bone cortex E wholly circumscribing deeper bone F and the arrow therein shown depicts the direction of its insertion into the bone. FIG. 26 shows wedge components 14 and 15 of the invention after having been pushed with the insertion tool into the hole previously drilled in bone and the arrow therein shown depicts the direction of removal of guide wire 13 once wedge components 14 and 15 are positioned in the hole previously drilled in bone. At this juncture, it should be noted that proximal wedge 14 and distal wedge 15, previously threaded with suture thread B as described above and repositioned on guide wire 13 below an insertion tool after guide wire 13 would have first been threaded through a cannulated drill bit into a hole drilled in bone and the cannulated drill bit removed from the hole and slipped up and off guide wire 13, are ready for permanently wedged insertion into the hole drilled in bone by way of the combined actions of pushing down on the head 1 of proximal wedge 14 in-situ with the insertion tool while at the same time pulling up on suture thread B. FIG. 27 shows the left thumb G and left index finger H of a surgeon pushing down on the head 1 of proximal wedge 14 with the insertion tool with downward force and FIG. 27 also shows the right thumb I and right index finger J of the surgeon beginning to pull on the two strands of suture thread B that were previously shown passing through suture entry hole 7 of distal wedge 15 out its suture exit hole 8 passing therefrom along its inclined base face 12 and back through its suture re-entry hole 8a of and up through the distal wedge 15 and out its suture re-exit hole 7a. Inclined base face 12 of the distal wedge 15 serves to prevent suture thread B from coming into contact with guide wire 13 as it would be emanating from hole 4c in the base of distal wedge 15. FIG. 28 shows the same digits of the same surgeon pushing down with the insertion tool on head 1 of proximal wedge 14 and simultaneously pulling on suture thread B. FIG. 29 shows how the two wedge components 14 and 15 of the invention are positioned together and firmly anchored within the hole previously drilled in bone once the surgeon has completed the above-described process of pushing and pulling. FIG. 30 is a blown up view of the inserted wedge components 14 and 15 of the instant invention. The arrows M, N and O depict how force emanantes laterally against the walling of the hole drilled in bone as a result of downward force L applied to head 1 of proximal wedge 14 being combined with upward force K due to the pulling up on the strands of suture thread B. The combined pushing and pulling causes the plurality of serrated edges of lateral side 2 of proximal wedge 14 to bite firmly into the bone adjacent thereto in view of the resultant upward sliding action of distal wedge 15 against proximal wedge 14 whereby the inclined face 6 of proximal wedge 14 previously in apposition to the medial aspect of distal wedge 15 comes into interfaced contact with the inclined face 11 of the distal wedge 15 such that the central diameter of the two wedge components 14 and 15 in apposition to one another is significantly increased. Also, beveled top side 9 of distal wedge 15 cuts into bone in apposition to it in response to such concomitant pushing and pulling to thereby contribute to anchoring and beveled top side 9 together with stop face 5 of proximal wedge 14 and stop face 10 of distal wedge 15 serve to prevent either wedge from sliding by the other during the application of forces L and K to thereby serve to defeat the intended purpose of increasing the central diameter of the two wedge components 14 and 15 in apposition to one another which increasing of the central diameter is what causes the laterally directed biting and cutting described above which in turn is responsible for the permanent positioning in the hole drilled in bone of wedge components 14 and 15 of the invention, to thus result in a firmly and permanently situated suture anchor in bone. FIG. 31 shows human or other animal soft tissue P held fast to bone by suture thread B tied thereabout such tissue P and concomitantly threaded through and about the distal wedge component 15 of the firmly and permanently situated instant suture anchor.

What is claimed is:

1. A suture anchor comprising:
   a. a flexible guide wire;
   b. a first wedge with four sides;
   c. a second wedge with four sides;
   d. a first side of the body of said first wedge made up of a plurality of serrated edges the long axes of each of which said serrated edges are perpendicular to the long axis of such first side;
   e. a cylindrically shaped head atop of and adjoined to the said body of said first wedge;
   f. a first round hole centered on the central axis of said head and said body;
   g. a second round hole centrally located in the lower portion of a second side of said body of said first wedge positioned opposite to the position of said first side, the plane of which said lower portion is inclined toward the direction of the said long axis of said first side;
   h. a canal leading from said first round hole to said second round hole;
   i. a stop face extending outwardly from and at an angle obtuse to the top edge of said lower portion of said second side which said stop face demarcates the junction of said lower portion of said second side and the upper portion of said second side;
   j. two identical cylindrically shaped grooves parallel to one another in said upper portion of said second side extending from the top edge of said second side to the locus of said stop face with the long central axis of each of said two grooves directed perpendicular to the top edge of said second side which is also the top edge of said body such that the distance from one first end of said top edge to the long central axis of the one of said two grooves nearest to said one first end equals, the distance from the other end of said top edge to the long central axis of the other of said two grooves;
   k. a beveled top edge of said second wedge the angle of bevel of which tapers to zero degrees at both ends of said top edge which said angle of bevel is obtusely inclined to the plane of a first side of said second wedge;
   l. two identical third and fourth holes positioned in the upper portion of a second side of said second wedge which said second side is opposite in position to that of said first side of said second wedge, each of which said third hole and said fourth hole are positioned parallel to each other with the horizontal central axis each of said third hole and said fourth hole being perpendicular in direction to the direction of the top line of said top edge of said second wedge and with each said horizontal central respectively equidistant from each one of the said ends of said top edge of said second wedge;
   m. a second wedge stop face extending outwardly from and at an angle obtuse to the plane of said upper portion of said second side of said second wedge, the inner edge of which said stop face is the bottom boundary line of said upper portion of said wedge;
   n. a lower portion of said second side of said second wedge extending from the outer edge of said second wedge stop face to the base of said second wedge;
   o. a fifth hole centrally positioned in said upper portion of said second side of said second wedge and centrally positioned in said second wedge stop face;
   p. a sixth hole located in the base of said second wedge;
   q. a canal leading from said fifth hole through the body of said second wedge to said sixth hole;
   r. an upwardly inclined portion of said base of said second wedge, the bottom boundary line of which said upwardly inclined portion abuts the circumference of said sixth hole and extends from the bottom of said second wedge's third side to the bottom of said second wedge's fourth side opposite in position to said third side and the upper boundary line of which said upwardly inclined portion constitutes the bottom boundary line of said first side of said second wedge;
   s. two identically shaped circular holes in said upwardly inclined portion of said base of said second wedge, the centers of each of which said holes are respectively equidistant from the center of said sixth hole;

t. two identical canals coursing through the body of said second wedge in directions parallel to one another leading one each respectively from one of each of said two identical third and fourth holes to one of each of said two identically shaped circular holes;

u. means for temporarily fastening said first wedge and said second wedge to said guide wire after said guide wire has been threaded through said firt round hole and said second round hole in said first wedge and said fifth hole and said sixth holein said second wedge.

2. A method for anchoring soft tissue to bone comprising the following steps:

a. constructing a four sided first wedge with a cylindrically shaped head atop of and adjoined to the body of said first wedge, a first round hole centered on the central axis of said head and said body, a plurality of serrated edges on a first side of said body, the long axes of each of which are perpendicular to the long axis of said first side, a second round hole centrally located in the lower portion of a second side of said body of said first wedge positioned opposite to the position of said first side, the plane of which said lower portion of said second side is inclined toward the direction of the said long axis of said first side; a canal leading from said first round hole to said second round hole; a stop face extending outwardly from and at an angle obtuse to the top edge of said lower portion of said second side which said stop face demarcates the junction of said lower portion of said second side and the upper portion of said second side; two identical cylindrically shaped grooves parallel to one another in said upper portion of said second side extending from the top edge of said second side to the locus of said stop face with the long central axis of each of said two grooves directed perpendicular to the top edge of said body which is also the top edge of said body such that the distance from one first end of said top edge to the long central axis of the one of said two grooves nearest to said one first end equals the distance from the other end of said top edge to the long central axis of the other of said two grooves;

b. constructing a four sided second wedge with a beveled top edge of said second wedge the angle of bevel of which tapers to zero degrees at both ends of said top edge with said angle of bevel is obtusely inclined to the plane of a first side of said second wedge and with two identical third and fourth holes positioned in the upper portion of a second side of said second wedge which said second side is opposite in position to that of said first side of said second wedge, each of which said two identical third and fourth holes are positioned parallel to each other with the horizontal central axis of each of said two identical third and fourth holes perpendicular in direction to the direction of the top line of said top edge of said second wedge and with each said horizontal central axis respectively equidistant from each one of the said ends of said top edge of said second edge; a second wedge stop face extending outwardly from and at an angle obtuse to the plane of said upper portion of said second side of said second wedge, the inner edge of which said stop face is the bottom boundary line of said upper portion of said second of said second wedge; a lower portion of said second side of said second wedge extending from the outer edge of said second wedge stop face to the base of said second wedge; a fifth hole centrally positioned in said upper portion of said second side of said second wedge and centrally positioned in said second wedge stop face; a sixth hole located in the base of said second wedge; a canal leading from said fifth hole through the body of said second wedge to said sixth hole; an upwardly inclined portion of said base of said second wedge, the bottom boundary line of which said upwardly inclined portion abuts the circumference of said first circular shaped hole and extends from the bottom of said second wedge's third side to the bottom of said second wedge's fourth side and opposite in position to said third side and the upper boundary line of which said upwardly inclined portion constitutes the bottom boundary line of said first side of said second wedge; two identically shaped circular holes in said upwardly inclined portion of said base of said second wedge, the centers of each of which said holes are respectively equidistant from the center of said sixth hole; two identical canals coursing through the body of said second wedge in directions parallel to one another leading one each respectively from one of each of said two identical third and fourth holes to one of each of said two identically shaped circular holes;

c. temporarily fastening said first wedge and said second wedge to a flexible guide wire after said guide wire has been threaded through said first round hole and said second round hole in said first wedge and said fifth hole said sixth hole in said second wedge;

d. threading suture material sufficiently through said identical third and fourth holes and said two identically shaped circular holes in said upwardly inclined portion of said base of said second wedge to permit the ends of said suture material to both be well beyond the lumens of said identical third and fourth holes;

e. drilling a hole into bone;

f. passing said guide wire into said hole in bone;

g. running said first wedge and said second wedge down said guide wire into said hole in bone;

h. removing said guide wire from said first wedge and said second wedge in said hole in bone;

i. pushing down forcefully on the said head of said first wedge while simultaneously pulling up forcefully on the said ends of said threaded suture material;

j. stitching human soft tissue bone with the said ends of said threaded suture material.

* * * * *